United States Patent [19]

Fenyes

[11] Patent Number: 4,801,362

[45] Date of Patent: Jan. 31, 1989

[54] CONTROL OF MICROORGANISMS IN AQUEOUS SYSTEMS WITH 1-HYDROXYMETHYLPYRAZOLES

[75] Inventor: Joseph G. Fenyes, Germantown, Tenn.

[73] Assignee: Buckman Laboratories International, Inc., Memphis, Tenn.

[21] Appl. No.: 131,733

[22] Filed: Dec. 11, 1987

[51] Int. Cl.$^4$ ............... C10M 133/44; C10M 173/02
[52] U.S. Cl. ................... 252/51; 252/33.6; 252/49.3; 252/49.5; 252/51.5 R; 106/3; 106/271; 106/272
[58] Field of Search ............ 252/49.3, 49.5, 51.0; 106/271, 272, 3

[56] References Cited

PUBLICATIONS

Dvoretzky et al., Formaldehyde Condensation in the Pyrazole Series, 15 Journ. Org. Chem., 1285–1288, (1952).
Huttel et al., Mannichsche Reaktion der Pyrazole, 85 Chemische Berichte 820–826, (1952). (original and English language abstract).
Hartbrich et al., "Reagent Combination for Preventing and/or Conf. Rolling the Nitrification of Ammonium Nitugen in Cultivated Soils", CA 103(21): 177558j.

*Primary Examiner*—William R. Dixon, Jr.
*Assistant Examiner*—Ellen McAvoy
*Attorney, Agent, or Firm*—Finnegan, Henderson, Farabow, Garrett & Dunner

[57] ABSTRACT

A method of preserving an aqueous system which is susceptible to microbiological degradation. To the system is added a compound having the formula

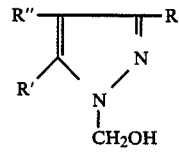

wherein R and R' are independently selected from hydrogen or a methyl group, R" is a moiety selected from the group consisting of (a) hydrogen, (b) a halogen atom selected from the group consisting of F, Cl, Br and I, and (c) a nitro group; or the hydrochloride salt of the compound. The method disclosed is especially useful for preserving aqueous solutions, emulsions, and suspensions which are susceptible to microbiological degradation.

13 Claims, No Drawings

CONTROL OF MICROORGANISMS IN AQUEOUS SYSTEMS WITH 1-HYDROXYMETHYLPYRAZOLES

FIELD OF THE INVENTION

The subject of the present invention is a method for the preservation of aqueous systems which are susceptible to microbiological degradation. Typical such systems include aqueous solutions, emulsions and suspensions.

BACKGROUND OF THE INVENTION

A large number of commercial and industrial products comprise aqueous systems containing organic materials. Examples are latexes, surfactants, dispersants, stabilizers, thickeners, adhesives, starches, waxes, proteins, emulsifying agents, detergents, cellulose products, and resins formulated in aqueous solutions, emulsions or suspensions. Such products frequently contain relatively large amounts of water. The temperature at which these products are stored, as well as their pH, makes these products susceptible to the growth of microorganisms. These microorganisms can be introduced during the manufacturing of these products (from exposure to air, tanks, pipes, equipment, and humans), and/or during their use (from multiple openings and reclosures of packaged products, and introduction of contaminated objects to stir or remove material).

Microbiological degradation of aqueous systems containing organic material may manifest itself in a variety of problems. These include loss of viscosity, gas formation, objectionable odors, decreased pH, emulsion breaking, color change, and gelling.

DESCRIPTION OF THE INVENTION

The present invention provides a method for the preservation of an aqueous system which is susceptible to microbiological degradation, comprising the step of adding to the system a compound having the formula

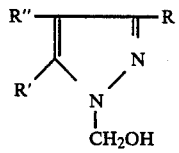

wherein R and R' are independently selected from hydrogen or a methyl group, R" is a moiety selected from the group consisting of (a) hydrogen, (b) a halogen atom selected from the group consisting of F, Cl, Br and I, and (c) a nitro group; or the hydrochloride salt of said compound, and wherein the compound or the hydrochloride salt of the compound is added in an amount sufficient to inhibit the growth and proliferation of at least one microorganism in the aqueous system.

The method of this invention may be used to prevent microbiological degradation in any aqueous system susceptible to such degradation, such as aqueous solutions, emulsions and suspensions.

Examples of aqueous solutions, emulsions, and suspensions which are subject to microbiological degradation include water-based paints, latex emulsions, such as acrylic and polyvinyl acetate emulsions, adhesive solutions and emulsions, wax emulsions, polishes, metalworking fluid solutions and emulsions, caulking and sealant products, papermaking chemical products such as alum solutions, clay and pigment dispersions, starch slurries and solutions, and protein coating formulations, and cosmetic preparations.

The preservative activity of the compounds of the invention is surprising insofar as N-methylol compounds of similar stability, for example N-hydroxymethylphthalimide, are not very effective in regard to their antimicrobial and preservative activity.

The compounds of this invention may be prepared by reacting either solid paraformaldehyde or an aqueous formaldehyde solution with a pyrazole derivative. Preferred methods of preparation are given in Dvoretzky et al., *Formaldehyde Condensation in the Pyrazole Series*, 15 Journ. Org. Chem. 1285-8 (1952) and Huttel et al., *Mannichsche Reaktion der Pyrazole*, 85 Chemische Berichte 820-26 (1952), both incorporated herein by reference.

The antimicrobial activity of the compounds used in accordance with the invention extends to a variety of different microorganisms, including bacteria such as *Escherichia coli, Staphylococcus aureus, Pseudomonas aeruginosa, Enterobacter aerogenes,* and *Bacillus subtilis,* and fungi such as *Candida albicans* and *Aspergillus niger.*

The concentration of the compounds of this invention which inhibits growth and proliferation of a microorganism, and thus provides the preservative effect described herein, may be readily determined by one skilled in the art without extensive experimentation and, preferably, will range from about 0.1 parts to about 1000 parts of the compound for one million parts of the aqueous system to be preserved.

To illustrate the nature of the invention, the following examples are given. It should be understood, however, that the invention is not to be limited to the specific conditions or details set forth in these examples.

EXAMPLE 1

The preservative effectiveness of these compounds was determined in a freshly prepared water-based paint formulated with titanium dioxide and calcium carbonate as pigments, an acrylic resin emulsion, dispersants, and hydroxyethyl cellulose as a thickener. The pH of this paint was approximately 9.0. The test was conducted as follows:

3,5-Dimethyl-1-hydroxymethylpyrazole was added to the completed acrylic latex paint at levels ranging from 75 to 1500 parts per million parts of the paint. One hundred grams of the test paint were inoculated weekly in a ten week challenge test with 1.0 milliliter of paint containing Pseudomonas aeruginosa at a level of approximately $1.5 \times 10^6$ organisms per milliliter. After vigorous shaking, the inoculated paint was incubated at 28° C. The test paints were streaked onto nutrient agar plates 24, 48, and 168 hours after inoculation. The streaked plates were incubated at 37° C. and examined for bacterial growth after 48 hours. Table I represents the final data accumulated from a ten week challenge test with paints containing 75 to 1500 parts of 3,5-dimethyl-1-hydroxymethylpyrazole per million parts of paint.

TABLE I

| Concentration of Product (ppm) | Test Results* at | | |
|---|---|---|---|
| | 24 h | 48 h | 168 h |
| 0 (control) | 3 | 3 | 3 |
| 75 | 3 | 3 | 3 |
| 100 | 3 | 3 | 3 |
| 150 | 3 | 3 | 3 |

TABLE I-continued

| Concentration of Product (ppm) | Test Results* at | | |
|---|---|---|---|
| | 24 h | 48 h | 168 h |
| 200 | 3 | 3 | 3 |
| 250 | 0 | 0 | 0 |
| 300 | 2 | 0 | 0 |
| 500 | 0 | 0 | 0 |
| 700 | 0 | 0 | 0 |
| 1000 | 0 | 0 | 0 |
| 1500 | 0 | 0 | 0 |

*KEY:
0 = No growth
1 = 1 colony
2 = 2 to 10 colonies
3 = over 10 colonies

EXAMPLE 2

The antimicrobial effectiveness of 1-hydroxymethylpyrazole, 3,5-dimethyl-1-hydroxymethylpyrazole, 3,5-dimethyl-1hydroxymethylpyrazole hydrochloride, and 4-chloro-3,5-dimethyl-1-hydroxymethylpyrazole was determined by the method for the preservation of an organic substance described in the United States Pharmacopeia, 21st revision (January 1, 1985), "Microbiological Test #51" p. 1151. Test results are given in Table II.

TABLE II

| Compound | Minimum Inhibitory Concentration (ppm) vs. | | | | |
|---|---|---|---|---|---|
| | E. coli | S. aureus | P. aeruqinosa | C. albicans | A. niger |
| 3,5-Dimethyl-1-hydroxymethylpyrazole | 100 | 250 | 100 | 50–100 | 25–50 |
| 1-Hydroxymethyl-pyrazole | 100 | 100 | 100 | 50–100 | 50–100 |
| 4-Chloro-3,5-dimethyl-1-hydroxmethylpyrazole | 50–100 | 50 | 50 | 1000–3000 | 100–500 |
| 3,5-Dimethyl-1-hydroxymethylpyrazole hydrochloride | 100 | 100 | 100 | 1000–3000 | 100–500 |

We claim:

1. A method of preserving an aqueous system which is susceptible to microbiological degradation, comprising the step of adding to said system a compound having the formula

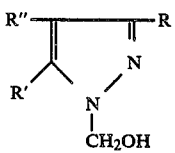

wherein R and R' are independently selected from hydrogen or a methyl group, R" is a moiety selected from the group consisting of (a) hydrogen, (b) a halogen atom selected from the group consisting of F, Cl, Br and I, and (c) a nitro group; or the hydrochloride salt of said compound, and wherein said compound or said hydrochloride salt of said compound is added in an amount sufficient to inhibit the growth and proliferation of at least one microorganism in said aqueous system.

2. The method of claim 1, wherein said aqueous system is selected from the group consisting of aqueous solutions, emulsions and suspensions.

3. The method of claim 1, wherein said compound is 3,5-dimethyl-1-hydroxymethylpyrazole.

4. The method of claim 1, wherein said hydrochloride salt of said compound is 3,5-dimethyl-1-hydroxymethylpyrazole hydrochloride.

5. The method of claim 1, wherein said aqueous system is a water-based paint.

6. The method of claim 1, wherein said aqueous system is a water-based paint and said compound is 3,5-dimethyl-1-hydroxymethylpyrazole.

7. The method of claim 1, wherein said aqueous system is a water-based paint and said hydrochloride salt of said compound is 3,5-dimethyl-1-hydroxymethylpyrazole hydrochloride.

8. The method of claim 1, wherein said aqueous system is a cosmetic preparation.

9. The method of claim 1, wherein said aqueous system is a cosmetic preparation and said compound is 3,5-dimethyl-1-hydroxymethylpyrazole.

10. The method of claim 1, wherein said aqueous system is a cosmetic preparation and said hydrochloride salt of said compound is 3,5-dimethyl-1-hydroxymethylpyrazole hydrochloride.

11. The method of claim 1, wherein said aqueous system is a metalworking fluid.

12. The method of claim 1, wherein said aqueous system is a metalworking fluid and said compound is 3,5-dimethyl-1-hydroxymethylpyrazole.

13. The method of claim 1, wherein said aqueous system is a metalworking fluid and said hydrochloride salt of said compound is 3,5-dimethyl-1-hydroxymethylpyrazole hydrochloride.

* * * * *

UNITED STATES PATENT AND TRADEMARK OFFICE
CERTIFICATE OF CORRECTION

PATENT NO. : 4,801,362
DATED : January 31, 1989
INVENTOR(S) : Joseph G. Fenyes

It is certified that error appears in the above-identified patent and that said Letters Patent is hereby corrected as shown below:

Column 2, line 51

"Pseudomonas aeruginosa" should be italicized.

Column 2, line 52

"106" should read "$10^6$".

Signed and Sealed this

Twenty-seventh Day of June, 1989

Attest:

DONALD J. QUIGG

*Attesting Officer*  *Commissioner of Patents and Trademarks*